US009492256B1

(12) United States Patent
Alotaibi et al.

(10) Patent No.: US 9,492,256 B1
(45) Date of Patent: Nov. 15, 2016

(54) REUSABLE BITE-RECORDING KIT FOR DENTAL IMPLANTS

(71) Applicant: King Saud University, Riyadh (SA)

(72) Inventors: Hanan N. S. Alotaibi, Riyadh (SA); Sulieman S. A. Al-Johany, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/003,749

(22) Filed: Jan. 21, 2016

(51) Int. Cl.
*A61C 19/05* (2006.01)
*A61C 8/00* (2006.01)

(52) U.S. Cl.
CPC ............. *A61C 19/05* (2013.01); *A61C 8/0087* (2013.01); *A61C 8/0089* (2013.01)

(58) Field of Classification Search
CPC ...... A61C 8/001; A61C 19/05; A61C 9/002; A61C 8/005; A61C 13/34; A61C 8/0068; A61C 8/0075; A61C 8/0078; A61C 8/0089; A61C 8/0087
USPC ...................................... 433/70, 71, 13, 224
See application file for complete search history.

(56) References Cited

U.S. PATENT DOCUMENTS

| 4,624,639 A | 11/1986 | Wong |
| 5,597,303 A | 1/1997 | Simmons |
| 5,795,152 A | 8/1998 | Glatt |
| 5,947,736 A | 9/1999 | Behrend |
| 7,789,664 B1 * | 9/2010 | Toth .......................... A61C 8/00 433/213 |
| 2012/0052463 A1 | 3/2012 | Pollet |
| 2012/0202169 A1 | 8/2012 | Ryu et al. |
| 2013/0157217 A1 | 6/2013 | LeBeau |
| 2013/0203009 A1 | 8/2013 | Mutsafi et al. |

FOREIGN PATENT DOCUMENTS

KR           20070099257           10/2007

* cited by examiner

*Primary Examiner* — Nicholas Lucchesi
(74) *Attorney, Agent, or Firm* — Richard C. Litman

(57) ABSTRACT

The reusable bite-recording kit for dental implants includes one or more first bases, each of which is removably secured in a previously installed implant. The first bases have adjustably threaded rods extending therefrom, with contact fittings disposed upon the distal ends of the rods. Two second bases are removably secured in previously installed implants opposite the first bases. The second bases have plates at their distal ends, with the plates captured in a channel of an occlusal table. The table defines an occlusal plane. The rods of the first bases are adjusted to place their contact fittings just in contact with the occlusal plane of the occlusal table of the second bases, thus establishing the occlusal plane of the first bases for the manufacture of prosthetic teeth of proper height. This precludes the imprecise fittings that can occur using non-rigid elastomer materials.

20 Claims, 4 Drawing Sheets

REUSABLE BITE-RECORDING KIT FOR DENTAL IMPLANTS

BACKGROUND OF THE INVENTION

1. Field of the Invention

The present invention relates generally to dentistry, and particularly to a reusable bite-recording kit for dental implants providing both vertical and horizontal adjustment using a rigid, non-elastic modeling structure.

2. Description of the Related Art

Dental implants, i.e., the permanent installation of an anchor structure into the maxillary or mandibular bone structure, are relatively recent advances in the field of dentistry. Such implants and their prosthetic crown teeth are relatively maintenance free, generally requiring no more maintenance than natural teeth, as opposed to removable bridgework and dental plates. Accordingly, many candidates for prosthetic teeth opt for the permanent installation of implants and prosthetic teeth, as opposed to being fitted with removable bridgework or a dental plate(s).

Of course it is critical that the completed implant and prosthetic tooth closely fit with the surrounding teeth, particularly those of the opposite maxillary or mandibular arch. An artificial tooth that is too high or too low, misaligned with other teeth, or having some other fit problem, can result in a number of difficulties for the patient. Accordingly the actual process of fitting the implant, and particularly the prosthetic tooth installed on the implant, is conventionally a relatively tedious and labor intensive procedure. The conventional procedure involves the molding of a thick fluid resilient material, e.g., silicone, in and around the immediate vicinity of the implant after the bone and gingival structure have healed following implant installation. The patient is then instructed to bite down upon the fresh resilient material, and to hold the bite until it sets. The resulting impression is used to make a casting of a tooth or teeth that will fit closely with the adjacent teeth of the patient.

There are at least a few problems with this conventional process. One problem is that the silicone (or other elastomer material) has sufficient resilience even when completely cured that it can be difficult to get a truly accurate casting from the material. There is almost always at least some additional fine work required to adjust the fit of the prosthetic tooth or teeth resulting from this procedure, and quite often the initial prosthetic tooth or teeth must be discarded and a new mold taken. Of course the silicone or other resilient material can only be used once, as once the material has set it is of no use to any other patient with their unique relationship of teeth. While the resilient material used to make such dental castings is not particularly costly, it is somewhat more expensive than related materials used in non-medical fields due to the need for absolute sterility and non-toxicity. The single use of such material thus tends to drive up the cost of the implant procedure and other dental procedures (e.g., crowns, etc.) that use this molding or casting process.

A number of different procedures have been developed in the past for the installation of implants, abutments, and prosthetic teeth for permanent installation upon those implants and abutments. An example of such is found in Korean Patent Publication No. 20070099257 published on Oct. 9, 2007 to KJ Meditech Co., Ltd. This reference describes (according to the drawings and English abstract) a recording bite device that attaches temporarily to an underlying implant. The recording bite device includes an occlusal recess for resin or wax in order to make an impression of an opposed tooth or teeth.

Thus, a reusable bite-recording kit for dental implants solving the aforementioned problems is desired.

SUMMARY OF THE INVENTION

The reusable bite-recording kit for dental implants includes a series of rigid mechanical components that attach removably to preinstalled implants in the mouth of a patient. One set of components comprises one or more first posts or bases, somewhat like the abutments installed in implants for holding prosthetic teeth. Each of the first posts or bases has a blind threaded passage extending axially therein from the distal end thereof, i.e., the end opposite the implant attachment end. A cooperatively threaded rod or stud is adjustably installed in the threaded passage of the first post or base, with the rod having a larger diameter contact fitting on its exterior end. The first post or base is temporarily installed in the implant and the threaded rod is adjusted as required to adjust the occlusal spacing of the contact fitting with the second posts or bases, described below.

Each of two second posts or bases has a rod extending therefrom with a non-circular (e.g., rectangular) plate at its distal end. The plates reside in the channel of an occlusal table that captures the plates therein, permitting only lateral adjustment of the spacing between the second posts or bases. This assembly is installed in implants in the maxillary or mandibular jaw structure opposite the first posts or bases, with the occlusal table defining an occlusal plane. The threaded rods or studs of the first posts or bases are adjusted to position their contact fittings just in contact with the occlusal table of the second post or base assembly, thereby establishing the occlusal plane of the first posts or bases for the manufacture of prosthetic teeth of proper height.

The rigid nature of all of the components provides a positive means of precisely establishing the occlusal plane and thus avoiding inaccuracies resulting from the use of resilient elastomers in establishing the occlusal plane. Moreover, all of the components of the reusable bite-recording kit are formed of materials that can be autoclaved or otherwise sterilized without damage thereto, thus permitting the kit to be reused many times over.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
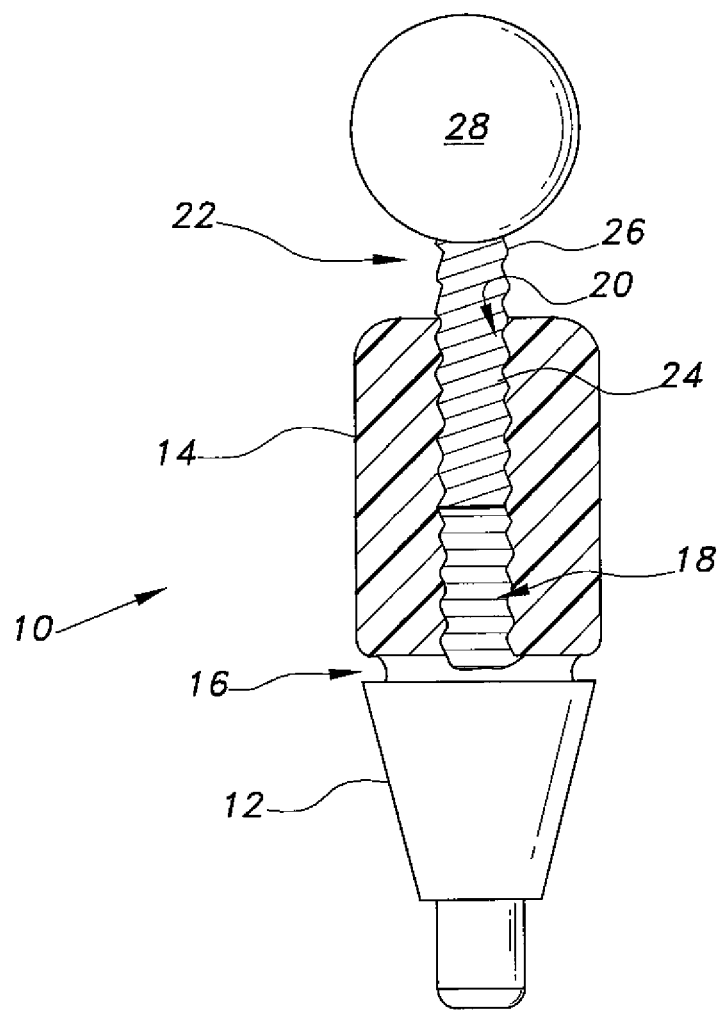
FIG. 1 is an elevation view in partial section of a first post or base of the reusable bite-recording kit for dental implants according to the present invention.

The reusable bite-recording kit for dental implants essentially comprises two assemblies that are removably installed upon implants that have been previously set in the opposite maxillary and mandibular jaw structures of the patient. FIG. 1 of the drawings illustrates an elevation view in section of a first assembly including a first jaw base 10, adapted for removable installation in a previously installed implant. The first jaw base 10 includes a conical implant portion 12, with a substantially cylindrical adjuster portion 14 extending opposite thereto, i.e., away from the bone structure in which the implant would have been set. The illustrated implant portion 12 is configured to fit securely with a corresponding Straumann® tissue level implant. It should be understood, however, that the implant portion 12 of the first base 10 may have any suitable geometric shape to cooperate closely with an implant, depending upon the internal shape of the implant socket. The implant portion 12 and adjuster portion 14 are separated by a circumferential groove 16 that can be disposed within the implant to secure the first jaw base 10 removably thereto.

An internally threaded adjuster passage 18 extends axially through the adjuster portion 14 from its distal end 20, i.e., the end opposite the implant portion 12. The adjuster passage 18 is a blind passage, i.e., it does not extend completely through the first jaw base 10. An occlusal height adjuster 22 comprises a cooperatively threaded adjuster rod 24 adjustably threaded into the adjuster passage 18 of the adjuster portion 14 of the first jaw base 10. The adjuster rod 24 has a distal end 26, i.e., the exposed end opposite the implant portion 12, with a contact fitting 28 disposed thereon. The contact fitting 28 is preferably a hard, rigid spherical ball, but may be alternatively shaped so long as the upper portion is radially symmetrical so as to preclude any differential in height of different portions of the upper surface of the contact fitting 28 as the adjuster rod 24 is rotated to adjust its height relative to the remainder of the first jaw base 10.

Figure 2:
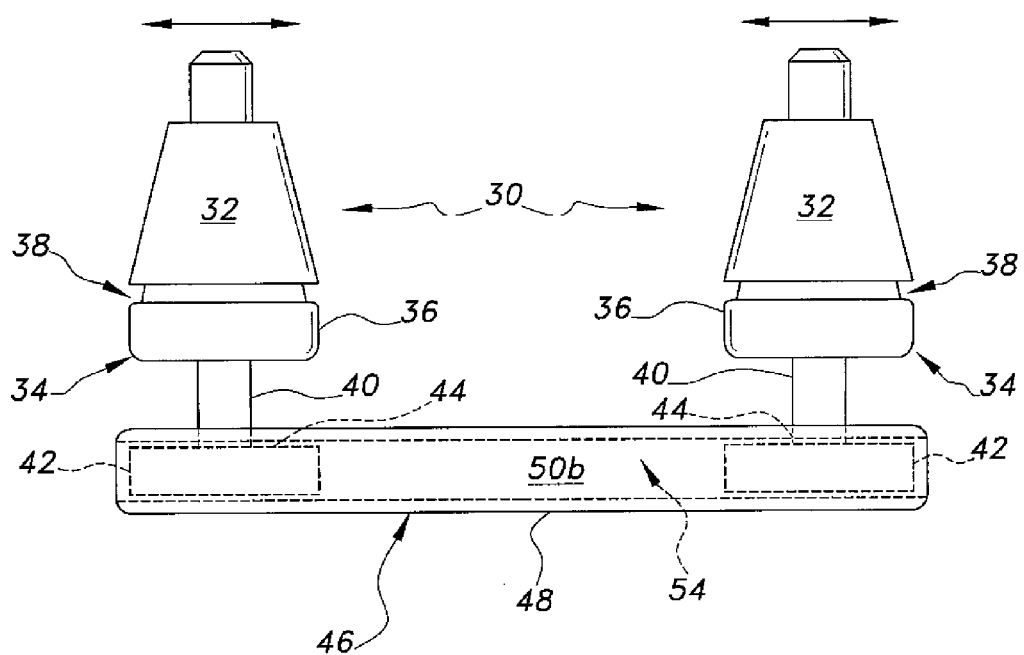
FIG. 2 is a side elevation view of an assembly including a pair of second posts or bases and occlusal table of the reusable bite-recording kit for dental implants according to the present invention.
Figure 3:
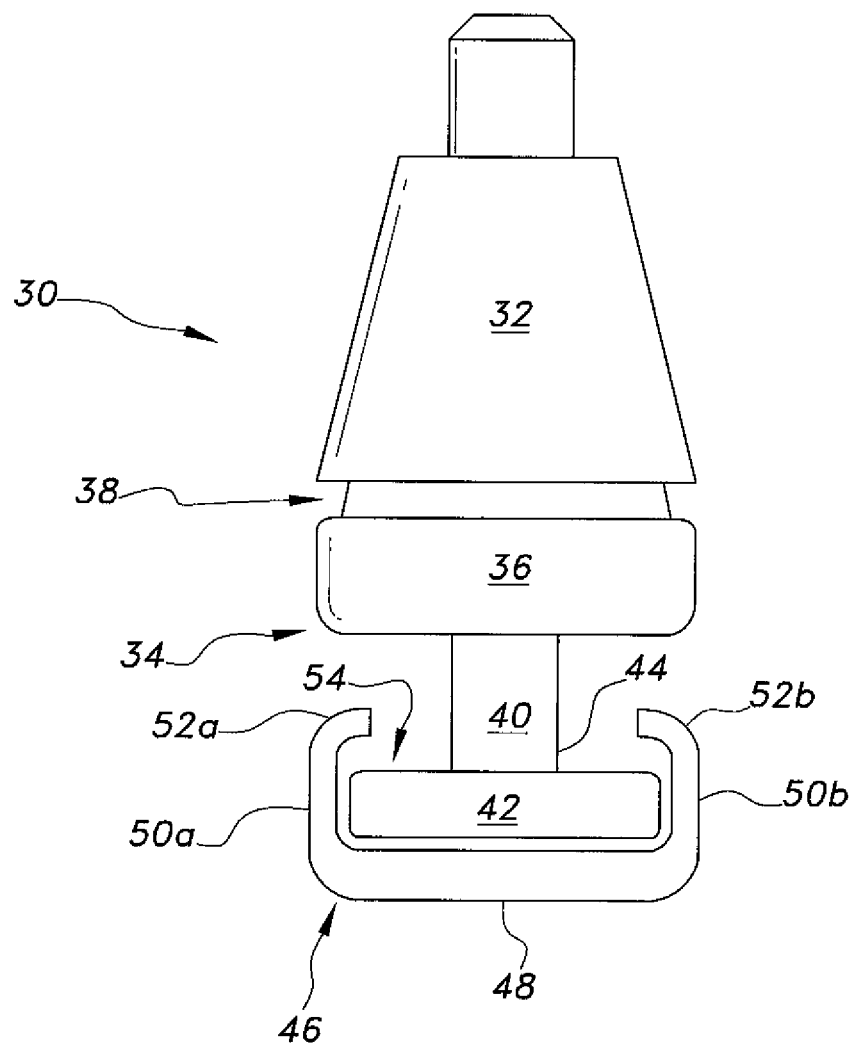
FIG. 3 is an end elevation view of the second posts or bases and occlusal table of FIG. 2.

FIGS. 2 and 3 provide elevation views of a second assembly including a pair of second jaw bases 30 adapted for removable installation in previously installed implants in the jaw structure opposite the jaw to which the first jaw base 10 is temporarily attached. It will be noted in the drawings that while the first jaw base 10 is oriented upward from a lower implant, the two second jaw bases 30 are oriented downward. This orientation would be the case if the first jaw base 10 were installed in an implant situated in the mandibular jaw structure and the second jaw bases 30 were installed in the maxillary jaw structure. However, it will be noted that this orientation may be reversed, with the first jaw base 10 removably attached to an implant in the upper or maxillary jaw structure and the second jaw bases 30 to implants in the lower or mandibular jaw structure, depending upon the configuration of the patient's jaw structure and the number of implants installed therein.

Each of the second jaw bases 30 has a conical (or other shape, depending upon the shape of the mating socket of the implant) implant attachment portion 32 with an occlusal table attachment 34 extending axially from the implant attachment portion 32. The occlusal table attachment 34 comprises a short cylindrical portion 36 separated from the implant attachment portion 32 by a circumferential groove 38, adapted to snap removably into the cooperating socket of an implant. A shaft 40 extends from the cylindrical portion 36, with a non-circular (e.g., square, rectangular, etc.) plate 42 disposed upon the distal end 44 of the shaft 40.

Figure 4:
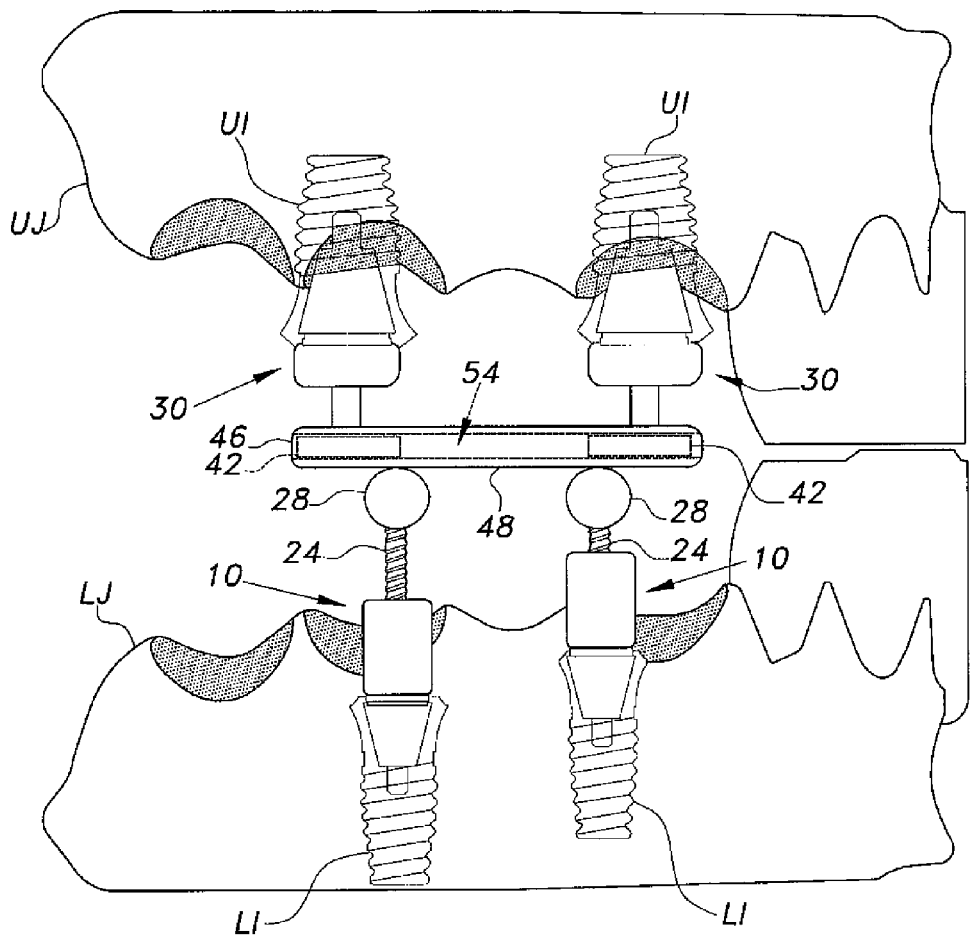
FIG. 4 is an environmental elevation view of the components of the reusable bite-recording kit for dental implants according to the present invention, showing the assembled components as they would be installed in a mouth.

A flat, elongate occlusal table 46 is provided, with the table 46 defining an occlusal plane and contact limit 48 for the occlusal height adjuster(s) 22 of the first jaw base(s) 10, generally as shown in FIG. 4 of the drawings and described further below. As shown more clearly in FIG. 3, the occlusal table 46 has laterally opposed first and second side walls, respectively 50a and 50b, with each of the side walls 50a, 50b having an inwardly extending lip, respectively 52a and 52b. The side walls 50a, 50b and lips 52a, 52b define a plate retaining channel 54, with the plates 42 of the occlusal table attachments 34 of the second jaw bases 30 being slidably captured within the channel 54.

FIG. 4 provides an environmental elevation view of an exemplary use of the reusable bite-recording kit for dental implants according to the present invention. In the example of FIG. 4, two of the first jaw base components 10 are shown temporarily installed in corresponding lower implants LI that have in turn been permanently installed in tooth sockets of the lower or mandibular jaw LJ of the patient. The pair of second jaw base components 30 is shown temporarily installed in corresponding upper implants UI that have in turn been permanently installed in tooth sockets of the upper or maxillary jaw UJ of the patient. The two plates 42 are slidably captured in the plate retaining channel 54 of the occlusal table 46, allowing the corresponding second jaw base components 30 to be adjustably spaced according to the distance between the upper implants UI in which they have been temporarily and removably installed. It will be seen that the relative height of the two second jaw base components 30 will depend upon the installations of their two corresponding upper implants UI, with the heights of the two plates 42 of the second jaw base components 30 thus defining the height of the occlusal plane and contact limit 48 of the occlusal table 46 attached to the two plates 42.

It will be noted that the two lower implants LI are set at different heights relative to one another, as often occurs due to the individual jaw structure of the patient. Accordingly, the adjuster rods 24 have been adjusted in order to position their corresponding contact fittings 28 so they are just in contact with the overlying occlusal plane 48 of the occlusal table 46 when the patient's mouth is fully closed. This will likely require some few adjustments of the adjuster rods 24, but once adjusted, the rigid structure of the various components accurately sets the heights of the contact fittings 28 so that prosthetic teeth of proper height may be manufactured. Much the same applies for the assembly of the two second jaw base components 30 and their plates 46.

As the various components comprising the reusable bite-recording kit for dental implants are adjustable to fit the specific bite of various patients, they need not be discarded after a single use as in the case of fluid materials that cure to form a resilient mass. Accordingly, the various components, i.e., the first jaw bases 10 and their occlusal height adjusters 22, the second jaw bases 30, and the occlusal table 46 are all formed of a rigid, non-resilient material such as a hard plastic (other materials that provide the same function may be used). Manufacture of the components from hard plastics capable of sustaining relatively high temperatures allows the components to be autoclaved or otherwise sterilized at high temperatures after use, thereby permitting the components to be reused multiple times.

It is to be understood that the present invention is not limited to the embodiments described above, but encompasses any and all embodiments within the scope of the following claims.

We claim:

1. A reusable bite-recording kit for dental implants, comprising:
at least one first jaw base having an implant attachment portion and a substantially cylindrical adjuster portion connected to the implant attachment portion;
an occlusal height adjuster adjustably positioned in the adjuster portion of the at least one first jaw base;
a pair of second jaw bases, each of the second jaw bases having an implant attachment portion and an occlusal table attachment extending axially from the implant attachment portion of each second jaw base; and
a flat, elongate occlusal table, the occlusal table defining an occlusal plane and contact limit for the occlusal height adjuster of the at least one first jaw base, each of the second jaw bases being adjustably captured in the occlusal table by means of the occlusal table attachment of each of the second jaw bases.

2. The reusable bite-recording kit for dental implants according to claim 1, wherein:
the adjuster portion of the at least one first jaw base has an axially disposed threaded adjuster passage therein; and
the occlusal height adjuster comprises a cooperatively threaded adjuster rod extending from the adjuster passage of the at least one first jaw base, the adjuster rod having a distal end opposite the at least one first jaw base with a contact fitting disposed upon the distal end of the adjuster rod.

3. The reusable bite-recording kit for dental implants according to claim 1, wherein:
the occlusal table has laterally opposed first and second side walls, each of the side walls having an inwardly extending lip, the side walls and lips defining a channel therebetween; and
the occlusal table attachment of each of the second jaw bases comprises an axially disposed shaft, the shaft having a distal end with a plate disposed thereon, the plate being slidably captured within the channel of the occlusal table.

4. The reusable bite-recording kit for dental implants according to claim 1, wherein each of the first jaw bases and second jaw bases have a groove disposed circumferentially therearound.

5. The reusable bite-recording kit for dental implants according to claim 1, wherein each of the first jaw bases, each of the second jaw bases, each occlusal height adjuster, and the occlusal table are formed of a rigid material.

6. The reusable bite-recording kit for dental implants according to claim 5, wherein the rigid material is a hard plastic.

7. The reusable bite-recording kit for dental implants according to claim 5, wherein each of the first jaw bases, each of the second jaw bases, each occlusal height adjuster, and the occlusal table are formed of reusable materials adapted for sterilizing between each use.

8. A reusable bite-recording kit for dental implants, comprising:
at least one first jaw base having an implant attachment portion and a substantially cylindrical adjuster portion connected to the implant attachment portion;
the adjuster portion of the first jaw base having an axially disposed threaded adjuster passage therein;
a cooperatively threaded adjuster rod extending from the adjuster passage of the at least one first jaw base, the adjuster rod having a distal end opposite the at least one first jaw base;
a contact fitting disposed upon the distal end of the adjuster rod;
a pair of second jaw bases, each of the second jaw bases having an implant attachment portion and an occlusal table attachment extending axially from the implant attachment portion of each second jaw base; and
a flat, elongate occlusal table, each of the second jaw bases being adjustably captured in the occlusal table by means of the occlusal table attachment of each of the second jaw bases.

9. The reusable bite-recording kit for dental implants according to claim 8, wherein the occlusal table defines an occlusal plane and contact limit for the occlusal height adjuster of the at least one first jaw base.

10. The reusable bite-recording kit for dental implants according to claim 8, wherein:
the occlusal table has laterally opposed first and second side walls, each of the side walls having an inwardly extending lip, the side walls and lips defining a channel therebetween; and
the occlusal table attachment of each of the second jaw bases comprises an axially disposed shaft, the shaft having a distal end with a plate disposed thereon, the plate being slidably captured within the channel of the occlusal table.

11. The reusable bite-recording kit for dental implants according to claim 8, wherein each of the first jaw bases and second jaw bases have a groove disposed circumferentially therearound.

12. The reusable bite-recording kit for dental implants according to claim 8, wherein each of the first jaw bases, each of the second jaw bases, each adjuster rod and contact fitting, and the occlusal table are formed of a rigid material.

13. The reusable bite-recording kit for dental implants according to claim 12, wherein the rigid material is a hard plastic.

14. The reusable bite-recording kit for dental implants according to claim 12, wherein each of the first jaw bases, each of the second jaw bases, each adjuster rod and contact fitting, and the occlusal table are formed of reusable materials adapted for sterilizing between each use.

15. A reusable bite-recording kit for dental implants, comprising:
at least one first jaw base having an implant attachment portion and a substantially cylindrical adjuster portion connected to the implant attachment portion;
an occlusal height adjuster extending from the adjuster portion of the at least one first jaw base;
a flat, elongate occlusal table, the occlusal table having laterally opposed first and second side walls, each of the side walls having an inwardly extending lip, the side walls and lips defining a channel therebetween; and
a pair of second jaw bases, each of the second jaw bases having an implant attachment portion and an occlusal table attachment extending axially from the implant attachment portion of each second jaw base, the occlusal table attachment of each of the second jaw bases comprising an axially disposed shaft, the shaft having a distal end with a plate disposed thereon, the plate being slidably captured within the channel of the occlusal table.

16. The reusable bite-recording kit for dental implants according to claim 15, wherein the occlusal table defines an occlusal plane and contact limit for the occlusal height adjuster of the at least one first jaw base.

17. The reusable bite-recording kit for dental implants according to claim 15, wherein:
- the adjuster portion of the at least one first jaw base has an axially disposed threaded adjuster passage therein;
- a cooperatively threaded adjuster rod extends from the adjuster passage of the at least one first jaw base, the adjuster rod having a distal end opposite the at least one first jaw base; and
- a contact fitting is disposed upon the distal end of the adjuster rod.

18. The reusable bite-recording kit for dental implants according to claim 15, wherein each of the first jaw bases and second jaw bases have a groove disposed circumferentially therearound.

19. The reusable bite-recording kit for dental implants according to claim 15, wherein each of the first jaw bases, each of the second jaw bases, each occlusal height adjuster, and the occlusal table are formed of a rigid material adapted for reuse and sterilizing between each use.

20. The reusable bite-recording kit for dental implants according to claim 19, wherein the rigid material is a hard plastic.

\* \* \* \* \*